United States Patent [19]
Weinberg et al.

[11] Patent Number: 5,759,546
[45] Date of Patent: Jun. 2, 1998

[54] TREATMENT OF CD4 T-CELL MEDIATED CONDITIONS

[76] Inventors: Andrew D. Weinberg, 3266 S.W. Fairmont Blvd., Portland, Oreg. 97201; Arthur A. Vandenbark, 4317 S.W. 48th Pl., Portland, Oreg. 97221

[21] Appl. No.: 192,480

[22] Filed: Feb. 4, 1994

[51] Int. Cl.$^6$ .............. C07K 16/28; C07K 19/00; A61K 39/395
[52] U.S. Cl. .................. 424/179.1; 424/184.1; 424/185.1; 530/387.1; 530/387.3; 530/388.75; 530/866; 530/867; 530/868
[58] Field of Search .............. 424/179.1, 184.1, 424/185.1; 530/387, 387.1, 387.3, 388.75, 868, 867, 866

[56] References Cited

U.S. PATENT DOCUMENTS

| | | |
|---|---|---|
| 4,590,071 | 5/1986 | Scannon et al. |
| 4,664,911 | 5/1987 | Uhr et al. |
| 4,681,760 | 7/1987 | Fathman |
| 4,731,244 | 3/1988 | Talle et al. |
| 4,867,973 | 9/1989 | Goers et al. ............ 424/85.91 |
| 5,045,451 | 9/1991 | Uhr et al. ............. 435/7.23 |
| 5,057,313 | 10/1991 | Shih et al. ............ 424/85.91 |
| 5,057,598 | 10/1991 | Pollack et al. .......... 530/387 |
| 5,091,177 | 2/1992 | Hellström et al. ....... 424/85.8 |
| 5,167,956 | 12/1992 | Neville et al. ......... 424/85.91 |

FOREIGN PATENT DOCUMENTS

| | | |
|---|---|---|
| 89/06967 | 10/1989 | WIPO. |
| WO 95/12673 | 5/1995 | WIPO. |

OTHER PUBLICATIONS

Miura et al., "Molecular Cloning and Characterization of a Novel Glycoprotein, gp34, That Is Specifically Induced by the Human T–Cell Leukemia Virus Type I Transactivator p40$^{tax}$, "Mol. Cell. Biol. 11:1313–1325 (1991).

W. Godfrey et al., 'Molecular cloning of a cDNA encoding the human homolog of the rat OX–40 antigen', p. 253, Tissue Antigens, vol. 42, No. 4, Oct. 1993, Copenhagen, Denmark.

S. Hamilton–Dutoit et al., 'An immunohistological analysis of the mAb in the activation antigen panel', p. 475 –p. 476, 'Leucocyte Typing IV. White Cell Differentiation Antigens (Eds. W. Knapp et al.)' 1989, Oxford University Press, Oxford, GB.

J. Waugh et al., 'Staining of normal or rejecting kidney using the activation panel', p. 485 –p. 486, 'Leucocyte Typing IV. White Cell Differentiation Antigens (Eds. W. Knapp et al.)' 1989, Oxford University Press, Oxford, GB.

N. Dunlap et al., 'Expression of activation antigens on HTLV–I and HTLV–II cell lines', p. 487 –p. 488, 'Leucocyte Typing IV. White Cell Differentiation Antigens (Eds. W. Knapp et al.)' 1989, Oxford, GB.

R. Vilella et al., 'Sequential appearance of the activation antigens',p. 495 –p. 498, 'Leucocyte Typing IV. White Cell Differentiation Antigens (Eds. W. Knapp et al.)' 1989, Oxford University Press, Oxford, GB.

G. Aversa et al., 'Activation panel antigen expression on PBL activated by PHA or in MLR', p. 498 –p. 501, 'Leucocyte Typing IV. White Cell Differentiation Antigens (Ed. W. Knapp et al.)' 1989, Oxford University Press, Oxford, GB.

P. King et al., 'Tonsillar dendritic–cell–induced T–lymphocyte proliferation: analysis of molecular mechanisms using the activation panel of mAb', p. 503 –p. 505, 'Leucocyte Typing IV. White Cell Differentiation Antigens (Eds. W. Knapp et al.)' 1989, Oxford University Press, Oxford, GB.

O. Rentrop et al., 'Biochemical analysis of the Workshop antibodies of the activation section', p. 473 –p. 474, 'Leucocyte Typing IV. White Cell Differentiation Antigens (Eds. W. Knapp et al.)' 1989, Oxford University Press, Oxford, GB.

U. Latza et al., 'The human OX40 homolog: cDNA structure, expression and chromosomal/assignment of the ACT35 antigen', pp. 677 –683, European Journal of Immunology, vol. 24, No. 3, Mar. 1994, Weinheim, Germany.

W. Godfrey, et al. 'Identification of a human OX–40 ligand, a costimulator of CD4+ T cells with homology to tumor necrosis factor', pp. 757 –762, The Journal of Experimental Medicine, vol. 180, N0. 2, Aug. 1994, New York NY, USA.

W. Godfrey et al., 'Stan–40, a new member of the FAS–TNFr superfamily expressed selectively on activated, human CD+ T cells', p. 355, Journal of Cellular Biochemistry, Supplement, vol. 0, No. 18D, 1994, New York NY, USA.

Caldherhead, et al., "Cloning of Mouse OX40: A T Cell Activation Marker That May Mediate T–B Cell Interactions," J. Immun. 151:5261–5271 (1993).

Holoshitz, et al., "Arthritis Induced in Rats by Cloned T Lymphocytes Responsive to Mycobacteria but Not to Collagen Type II," J. Clin. Invest. 73:211–215 (1984).

Kennedy, et al., "Analysis of Cytokine mRNA Expression in the Central Nervous System of Mice with Experimental Autoimmune Encephalomyelitis Reveals that IL–10 mRNA Expression Correlates with Recovery . " J. Immun. 149:2496–2505 (1992).

(List continued on next page.)

*Primary Examiner*—Frank C. Eisenschenk
*Attorney, Agent, or Firm*—Klarquist Sparkman Campbell Leigh & Whinston, LLP

[57] ABSTRACT

A method for the selective depletion of activated CD4$^+$ T-cells in vivo by using immunotoxins comprising the OX-40 antibody conjugated to a toxic molecule (such as Ricin-A chain). The administration of these specific immunotoxins is used therapeutically to deplete autoimmune reactive CD4$^+$ T-cells which have been implicated in diseases including Multiple Sclerosis, Rheumatoid Arthritis, Sarcoidosis, and Autoimmune Uveitis. This type of therapy is also beneficial for eradicating CD4$^+$ T-cell lymphomas and alloreactive CD4$^+$ T-cells involved with a transplantation reaction. The use of the human form of the OX-40 antibody will also help in the early diagnosis of all the diseases mentioned above.

23 Claims, 5 Drawing Sheets

OTHER PUBLICATIONS

Khoury, et al., "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor β, Interleukin 4, and Prostaglandin E Expression in the Brain," *J. Exp. Med.* 176:1355–1364 (1992).

Mallett, et al., "Characterization of the MRC OX40 Antigen of Activated CD4 Positive T Lymphocytes—a Molecule Related to Nerve Growth Factor Receptor," *Embo J.* 9:1063–1068 (1990).

Paterson, et al., "Antigens of Activated Rat T Lymphocytes Including a Molecule of 50,000$M_r$ Detected Only on CD4 Positive T Blasts," *Mol. Immun.* 24:1281–1290 (1987).

Steinman, Lawrence, "Autoimmune Disease," *Sci. Amer.* 9:107–114 (1993).

Vitetta, et al., "Phase I Immunotoxin Trial in Patients with B–Cell Lymphoma," *Cancer Res.* 51:4052–4058 (1991).

Weinberg, et al., "Transforming Growth Factor–β Enhances the in Vivo Effector Function and Memory Phenotype of Antigen–Specific T Helper Cells in Experimental Autoimmune Encephalomyelitis," *J. Immun.* 148:2109–2117 (1992).

Walmann, Monoclonal antibodies in diagnosis and therapy, Science, vol. 252, pp. 1657–1662, 1991.

Parker et al., Fusion Proteins in Immu notherapy, Trans. Proc. vol. 24, No. 6, pp. 2362–2365, 1992.

Queen et al. [Proc. Natl. Acad. Sci. 86:10029–10033 (1989)].

Lohse et al. [Springer Semin Immunopathol 14:179–186 (1992)].

Chatterjee et al. [Cancer Immunol. Immunother. 38:75–82 (1994)].

Harris et al. [Tib Tech 11:42–44 (1993)].

Emery et al. (Exp. Opin. Invest. Drugs, 1994.

Winter et al. [TIPS 14:139–143 (1993)].

Kahan [Cur. Opin. Immunol., (1992)].

Borrebaeck et al. [Immunol. Today, 1993).

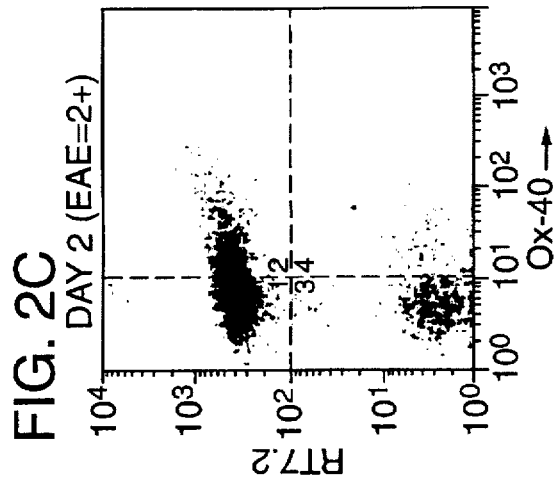
FIG. 2A DAY 0 (EAE=0)
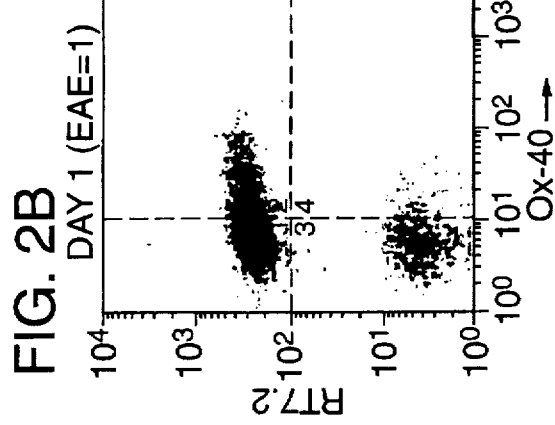
FIG. 2B DAY 1 (EAE=1)
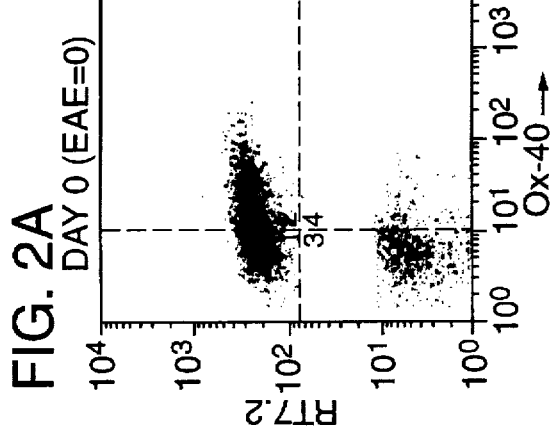
FIG. 2C DAY 2 (EAE=2+)
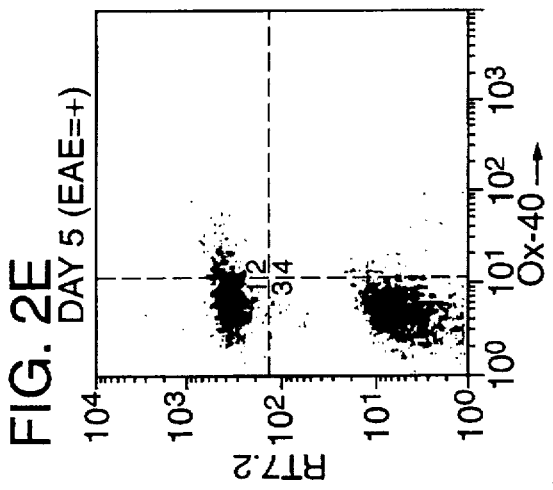
FIG. 2E DAY 5 (EAE=+)
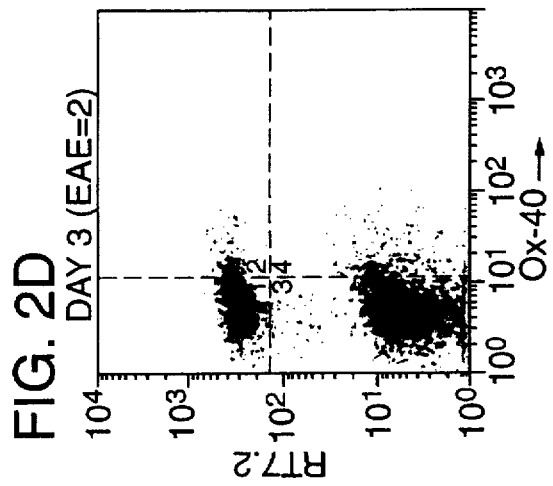
FIG. 2D DAY 3 (EAE=2)

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 848 base pairs
      ( B ) TYPE: Nucleic acid
      ( C ) STRANDEDNESS: Double
      ( D ) TOPOLOGY: Linear ( i i ) MOLECULE TYPE: cDNA to mRNA ( i i i ) HYPOTHETICAL: No ( i v ) ANTI-SENSE: No ( v ) FRAGMENT TYPE:

( x i ) SEQUENCE DESCRIPTION: SEQ ID NO: 1:

```
                                                         CGGC AGAGACGAGG       14

ATG TGC GTG GGG GCT CGG CGG CTG GGC CGC GGG CCG TGT GCG GCT      59
met cys val gly ala arg arg leu gly arg gly pro cys ala ala
 1               5                  10                  15

CTG CTC CTC CTG GGC CTG GGG CTG AGC ACC GTG ACG GGG CTC CAC     104
leu leu leu leu gly leu gly leu ser thr val thr gly leu his
                 20                  25                  30

TGT GTC GGG GAC ACC TAC CCC AGC AAC GAC CGG TGC TGC CAC GAG     149
cys val gly asp thr tyr pro ser asn asp arg cys cys his glu
                 35                  40                  45

TGC AGG CCA GGC AAC GGG ATG GTG AGC CGC TGC AGC CGC TCC CAG     194
cys arg pro gly asn gly met val ser arg cys ser arg ser gln
                 50                  55                  60

AAC ACG GTG TGC CGT CCG TGC GGG CCG GGC TTC TAC AAC GAC GTG     239
asn thr val cys arg pro cys gly pro gly phe tyr asn asp val
                 65                  70                  75
```

| | | | | | | | | | | | | | | | |
|---|---|---|---|---|---|---|---|---|---|---|---|---|---|---|---|
| GTC | AGC | TCC | AAG | CCG | TGC | AAG | CCC | TGC | ACG | TGG | TGT | AAC | CTC | AGA | 284 |
| val | ser | ser | lys | pro | cys | lys | pro | cys | thr | trp | cys | asn | leu | arg | |
| | | | 80 | | | | | 85 | | | | | | 90 | |
| AGT | GGG | AGT | GAA | CGG | AAG | CAG | CTA | TGC | ACG | GCC | ACA | CAG | GAC | ACA | 329 |
| ser | gly | ser | glu | arg | lys | gln | leu | cys | thr | ala | thr | gln | asp | thr | |
| | | | | 95 | | | | 100 | | | | | | 105 | |
| GTC | TGT | CGC | TGC | CGG | GCG | GGC | ACC | CAG | TCC | CTG | GAC | AGC | TAC | AAG | 374 |
| val | cys | arg | cys | arg | ala | gly | thr | gln | ser | leu | asp | ser | tyr | lys | |
| | | | | 110 | | | | 115 | | | | | | 120 | |
| CCT | GGA | GTT | GAC | TGT | GCC | CCC | TGC | CCT | CCA | GGG | CAC | TTC | TCC | CCA | 419 |
| pro | gly | val | asp | cys | ala | pro | cys | pro | pro | gly | his | phe | ser | pro | |
| | | | | 125 | | | | 130 | | | | | | 135 | |
| GGC | GAC | AAC | CAG | GCC | TGC | AAG | CCC | TGG | ACC | ACC | TGT | ACC | TTG | GTT | 464 |
| gly | asp | asn | gln | ala | cys | lys | pro | trp | thr | thr | cys | thr | leu | val | |
| | | | | 140 | | | | 145 | | | | | | 150 | |
| GGG | AAG | CAC | ACC | CTG | CAG | CCG | GCC | AGT | AAT | AGC | TCG | GAC | GCA | ATC | 509 |
| gly | lys | his | thr | leu | gln | pro | ala | ser | asn | ser | ser | asp | ala | ile | |
| | | | | 155 | | | | 160 | | | | | | 165 | |
| TGT | GAG | GAC | AGG | GAC | CCC | CCA | GCC | ACG | CAG | CCC | CAG | GAG | ACC | CAG | 554 |
| cys | glu | asp | arg | asp | pro | pro | ala | thr | gln | pro | gln | glu | thr | gln | |
| | | | | 170 | | | | 175 | | | | | | 180 | |
| GGT | CCC | CCG | GCC | AGG | CCC | ATC | ACT | GTC | CAG | CCC | ACT | GAA | GCC | TGG | 599 |
| gly | pro | pro | ala | arg | pro | ile | thr | val | gln | pro | thr | glu | ala | trp | |
| | | | | 185 | | | | 190 | | | | | | 195 | |
| CCC | AGA | ACC | TCA | CAG | GGA | CCC | TCC | ACC | CGG | TCC | GTG | GAG | GTC | CCC | 644 |
| pro | arg | thr | ser | gln | gly | pro | ser | thr | arg | ser | val | glu | val | pro | |
| | | | | 200 | | | | 205 | | | | | | 210 | |
| GGG | GGC | CGT | GCG | GTT | GCC | GCC | ATC | CTG | GGA | CTG | GGA | CTG | GTG | CTG | 689 |
| gly | gly | arg | ala | val | ala | ala | ile | leu | gly | leu | gly | leu | val | leu | |
| | | | | 215 | | | | 220 | | | | | | 225 | |
| GGG | CTG | CTG | GGA | CCC | CTG | GAC | ATC | CTG | CTG | GCC | CTG | TAC | CTG | ATC | 734 |
| gly | leu | leu | gly | pro | leu | asp | ile | leu | leu | ala | leu | tyr | leu | ile | |
| | | | | 230 | | | | 235 | | | | | | 240 | |
| CGG | AGG | GAC | CAG | AGG | CTG | CCC | CCC | GAT | GCC | CAC | AAG | CCC | CCT | GGG | 779 |
| arg | arg | asp | gln | arg | leu | pro | pro | asp | ala | his | lys | pro | pro | gly | |
| | | | | 245 | | | | 250 | | | | | | 255 | |
| GGA | GGT | AGC | TTC | CGG | ACC | CCC | ATC | CAA | GAG | GAG | CAG | GCC | GAC | GCC | 824 |
| gly | gly | ser | phe | arg | thr | pro | ile | gln | glu | glu | gln | ala | asp | ala | |
| | | | | 260 | | | | 265 | | | | | | 270 | |
| CAC | TCC | ACC | CTG | GTC | AAG | TTC | TGA | | | | | | | | 848 |
| his | ser | thr | leu | val | lys | phe | | | | | | | | | |
| | | | | 275 | | | | | | | | | | | |

( 2 ) INFORMATION FOR SEQ ID NO:2:

( i ) SEQUENCE CHARACTERISTICS:
        ( A ) LENGTH: 24 base pairs
        ( B ) TYPE: Nucleic acid
        ( C ) STRANDEDNESS: Single
        ( D ) TOPOLOGY: Linear ( i i i ) HYPOTHETICAL: No ( i v ) ANTI-SENSE: No ( x i ) SEQUENCE DESCRIPTION: SEQ ID NO: 2:

ATGTGCGTGG GGGCTCGGCG GCTG    24

( 2 ) INFORMATION FOR SEQ ID NO:3:

( i ) SEQUENCE CHARACTERISTICS:
        ( A ) LENGTH: 24 base pairs
        ( B ) TYPE: Nucleic acid
        ( C ) STRANDEDNESS: Single

```
        (  D  ) TOPOLOGY: Linear ( i i i ) HYPOTHETICAL: No (  i v  ) ANTI-SENSE: No (  x i  ) SEQUENCE DESCRIPTION: SEQ ID NO: 3:

TCAGAACTTG ACCAGGGTGG AGTG                                               2 4
```

TREATMENT OF CD4 T-CELL MEDIATED CONDITIONS

TECHNICAL FIELD

This invention relates to methods for the specific depletion of activated T-lymphocytes belonging to the $CD4^+$ subclass. Such activated $CD4^+$ T-lymphocytes are implicated in a number of conditions in humans including multiple sclerosis and transplant rejection. In particular, this invention provides a treatment in which activated $CD4^+$ T-lymphocytes involved in a particular disease or condition are depleted while the non-activated $CD4^+$ T-lymphocyte repertoire is unaffected.

BACKGROUND OF INVENTION

The $CD4^+$ T-lymphocyte (herein referred to as the $CD4^+$ T-cell) is the central player in the immune system because of the "help" it provides to other leukocytes in fighting off infection and potential cancerous cells. $CD4^+$ T-cells play essential roles in both humoral and cell-mediated immunity and additionally they act during parasite infection to promote the differentiation of eosinophils and mast cells. If the $CD4^+$ T-cell population is deleted (as is the case in AIDS patients) the host is rendered susceptible to a number of pathogens and tumors that do not ordinarily pose a threat to the host.

While $CD4^+$ T-cells thus play an important beneficial role in disease prevention, the aberrant function of these cells can produce serious problems. In some individuals, the aberrant function of $CD4^+$ T-cells leads to autoimmunity and other disease states (Swanborg, R. H., 1984; Cush, J. J., and Lipsky, P. E., 1988; Caspi et al., 1988). Autoimmune diseases in which $CD4^+$ T-cells have been implicated include multiple sclerosis, rheumatoid arthritis and autoimmune uveitis (see generally, Steinman, L., 1993). In essence these diseases involve an aberrant immune response in which the immune system is subverted from its normal role of attacking invading pathogens and instead attacks the host body tissues, leading to illness and even death. The targeted host tissues vary between autoimmune diseases, for example, in multiple sclerosis the immune system attacks the white matter of the brain and spinal cord, in rheumatoid arthritis the immune system attacks the synovial lining of the joints. Activated $CD4^+$ T-cells have also been implicated in other illnesses, including rejection of transplant tissues and organs and in the development of $CD4^+$ T-cell lymphomas.

Investigations into conditions caused by aberrant $CD4^+$ T-cell activity are focussed on several animal models, and in particular on a number of experimentally induced autoimmune diseases. Research on these experimentally induced diseases in animals is premised on the idea that they will provide information useful in the treatment of the corresponding human diseases. In pursuit of this goal, it has been shown that $CD4^+$ T-cells are responsible for several experimentally induced autoimmune diseases in animals, including experimental autoimmune encephalomyelitis (EAE), collagen induced arthritis (CIA), and experimental autoimmune uveitis (EAU).

EAE is induced by autoimmunizing animals against myelin basic protein (MBP, a component of the white matter of the brain and the spinal cord) and produces the same clinical symptoms observed in multiple sclerosis: demyelination and paralysis. Proof of the value of the EAE model as a comparative model for multiple sclerosis has been provided by evidence showing that these conditions share a causative nexus: Steinman and co-workers showed that the predominant cell type found in the brain lesions of multiple sclerosis patients is $CD4^+$ T-cells (Oksenberg, J. R., et al., 1990) and that the T-cell receptor (the molecule responsible for antigen recognition) associated with the cells in these brain lesions had the same 3 amino acid binding motif for antigen recognition as on the $CD4^+$ T-cells responsible for causing experimental autoimmune encephalomyelitis (EAE) (Oksenberg, J. R., et al., 1993).

All the evidence thus suggests that the EAE model will be useful in testing therapies for multiple sclerosis.

Research on a number of the experimentally induced autoimmune diseases, including EAE, CIA and EAU, has shown that antibodies that bind $CD4^+$ T-cells when injected in vivo can inhibit the development of these diseases as well as inhibit transplantation rejection (Swanborg, R. H. 1983; Cobbold, S. P. et al., 1984; Steinman, L. 1993). This antibody-mediated effect depletes or inactivates all $CD4^+$ cells in the body (the antibodies that bind to the $CD4^+$ cells presumably block the activity of the cells and also target the $CD4^+$ cells for destruction by the immune system.) This strategy has shown some success with rheumatoid arthritis and is now being tested for multiple sclerosis (see generally, Steinman, L., 1993).

While it appears that therapeutic approaches that destroy the $CD4^+$ T-lymphocyte population might be effective in ameliorating these autoimmune diseases, this approach has one very major drawback. The treatment not only destroys those $CD4^+$ T-cells that are antigen reactive and thus involved in the autoimmune disease process, but also the $CD4^+$ T-cells that are quiescent and not involved in the disease. Since $CD4^+$ T-cells are important in the general immune response (protecting the body against infectious agents), destruction of the entire $CD4^+$ T-cell population leaves the patient severely immunocompromised and hence highly susceptible to infection. A preferable approach would be to remove only those $CD4^+$ T-cells that are actively involved in the immune response, leaving the remaining $CD4^+$ T-cell population available for their normal role in the immune system.

This method of treatment has not yet been achieved. It is therefore an object of the present invention to provide a method of specifically depleting the population of activated $CD4^+$ T-cells in a patient without affecting the quiescent $CD4^+$ T-cell population.

SUMMARY OF THE INVENTION

The present invention provides a method by which autoantigen specific $CD4^+$ T-cells can be specifically eliminated in vivo, while leaving the quiescent population of $CD4^+$ T-cells intact. This invention therefore provides a treatment useful for $CD4^+$ T-cell mediated autoimmune diseases such as multiple sclerosis, rheumatoid arthritis, sarcoidosis and autoimmune uveitis. This invention also provides a method for eliminating other undesired immune responses caused by activated $CD4^+$ T-cells, such as rejection of transplanted tissue and organs in transplant recipients. Furthermore, the present invention provides a method of specifically eliminating activated $CD4^+$ T-cell lymphomas from the body. The present invention also provides a method for early diagnosis of conditions mediated by activated $CD4^+$ cells, by detecting the presence of autoreactive $CD4^+$ T-cells at the site of autoimmune lesions and potentially harmful $CD4^+$ T-cell lymphomas. This early diagnosis provides an indication that the methods of treatment provided by the present invention may be effective and can facilitate earlier treatment of the condition than might otherwise be possible.

The present invention is based on the discovery that a particular protein antigen, termed OX-40 (herein referred to as the OX-40 antigen), is specifically expressed on the surface of antigen activated CD4+ T-cells. In particular, using the EAE disease model in rats, this antigen was shown to be expressed on the surface of activated CD4+ T-cells present at the site of inflammation (the spinal cord in this disease model) but absent on CD4+ T-cells at non-inflammatory sites. Furthermore, the highest expression of this antigen on these CD4+ T-cells was found to occur on the day prior to initiation of clinical signs of autoimmunity; the expression of this antigen decreased as the disease progressed. The specificity of expression of the OX-40 antigen and the transient nature of this expression, shown for the first time in the present invention, motivated the testing of this antigen as a possible target for antibody mediated depletion of activated CD4+ T-cells in patients suffering from CD4+ T-cell mediated conditions.

Simply finding a target antigen on a particular cell type does not provide a basis for a therapeutic approach which requires depleting the particular cell type. Thus, many antigens are shed from the cell surface and are not suitable as targets for therapy. A second novel aspect of this invention is the discovery that an antibody raised against the OX-40 protein and conjugated to a cytotoxin can inhibit the in vitro proliferation of antigen activated CD4+ T-cells. This discovery implies that the OX-40 antigen is rapidly internalized by CD4+ T-cells. Additional research based on this discovery led to the main focus of the present invention; a demonstration that a population of antigen activated CD4+ T-cells can be depleted in vivo by conjugating an antibody raised against the OX-40 antigen with a cytotoxin to produce an immunotoxin, and administering this immunotoxin to a host. In this manner, the antibody binds to the OX-40 antigen on the surface of the activated CD4+ T-cell. Internalization of the immunotoxin results in the cytotoxin being taken into the cell, which produces cell death. Hence, administration of this immunotoxin to a host suffering from activated CD4+ T-cell mediated inflammation depletes (or otherwise inactivates) the activated CD4+ T-cells at the site of inflammation or other sites, leading to amelioration of subsequent inflammation.

One aspect of the present invention is therefore a method of treating a patient suffering from a condition mediated by activated CD4+ T-cells which comprises administering to the patient an effective amount of an antibody conjugated with a cytotoxic agent wherein the antibody recognizes and binds to the OX-40 antigen present on the surface of the CD4+ T-cells. This method is applicable to any condition mediated by antigen activated CD4+ T-cells, including, multiple sclerosis, sarcoidosis, rheumatoid arthritis, autoimmune uveitis, CD4+ T-cell lymphomas and rejection of a transplanted organ or tissue.

The methods of treatment set forth in the preceding paragraph will preferably be performed using monoclonal antibodies. In a more preferred embodiment, the monoclonal antibody will be a humanized monoclonal antibody. In alternative embodiments, the method will utilize a cytotoxic conjugate comprising a Fab, F(ab')$_2$ or Fv fragment of a monoclonal antibody conjugated with a cytotoxic agent wherein the fragment of the monoclonal antibody recognizes the OX-40 antigen.

This invention also encompasses monoclonal antibodies having a specificity of binding in cells to substantially only antigen activated CD4+ T-cells. In a preferred embodiment, this monoclonal antibody binds to the OX-40 antigen.

Another aspect of this invention is antibody-cytotoxin conjugates (also known as immunotoxins) suitable for use in the method of treatment described above.

A further aspect of the present invention is a method of detecting an inflammatory condition mediated by activated CD4+ T-cells in a patient by obtaining a suitable biopsy sample from the patient and then quantifying the percentage of activated CD4+ T-cells in the biopsy sample using an antibody that specifically binds to the OX-40 antigen. Other aspects of the present invention include test kits for detecting or treating conditions mediated by activated CD4+ T-cells.

These and other aspects of the present invention will become more readily apparent from the following figures and description of the invention.

DESCRIPTION OF THE DRAWINGS

FIGS. 2A–E show dot plots from a FACS apparatus showing a time course of OX-40 expression on donor T-cells isolated from the spinal cords of rats with EAE. Lymphocytes were isolated from the spinal cords of rats during the time course of disease. The cells were stained with the OX-40 antibody (FITC) and counterstained with a PE conjugated RT7.2 antibody. An isotype matched control antibody was used to draw the quadrants for both the FITC and PE conjugated Abs. The day of the EAE time course for each dot plot is indicated on the top of the graphs and the disease score (the severity of the clinical signs and disease score is provided in the methods section under "Adoptive Transfer of EAE") is shown in parenthesis next to the day of disease. The percentage of RT7.2+ cells were 77, 75, 81, 37, and 52% respectively for Days 0, 1, 2, 3, and 5 after disease onset. The OX-40 antibody was 54% positive for the donor T-cells on Day 0 (day before onset) and 41, 30, 18, and 12% positive on days 1, 2, 3, and 5 respectively. On Day 5 the EAE score of "+" means the animal had minimal clinical signs of paralysis (less than 1) but was not completely well.

FIG. 7 shows the nucleotide sequence of the coding region of the human OX-40 cDNA and the theoretical amino acid sequence of the human OX-40 antigen. These sequences are encompassed within SEQ I.D. No. 1 set forth in the accompanying sequence listing.

DETAILED DESCRIPTION OF THE INVENTION

Figure 1A:
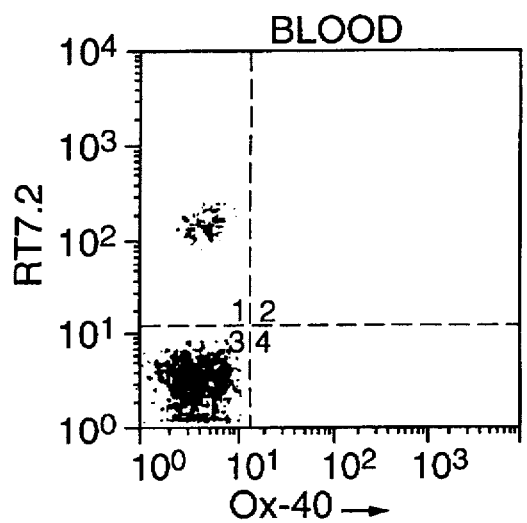
FIGS. 1A–D show dot plots from a fluorescence activated cell sorting (FACS) apparatus showing tissue specific dual expression of RT7.2 and the MRC OX-40 antigen. Lymphocytes were isolated from the various tissue compartments designated in the figures during the onset of EAE. The cells were stained with the OX-40 antibody conjugated to fluorescein isothiocyanate (FITC) displayed on the x-axis and counterstained with a R-phycoerythrin (PE) conjugated to the RT7.2 antibody displayed on the y-axis. An isotype matched control antibody was used to draw the quadrants for both the FITC and PE conjugated Abs. The OX-40 antibody was 50% positive on the donor T-cells isolated from the spinal cord, and 8, 2, and 1.8% positive for the donor cells isolated from the CSF, spleen, and blood respectively.
Figure 1B:
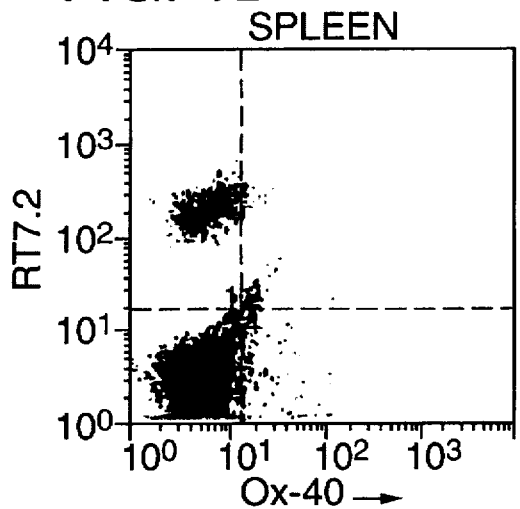
Figure 1C:
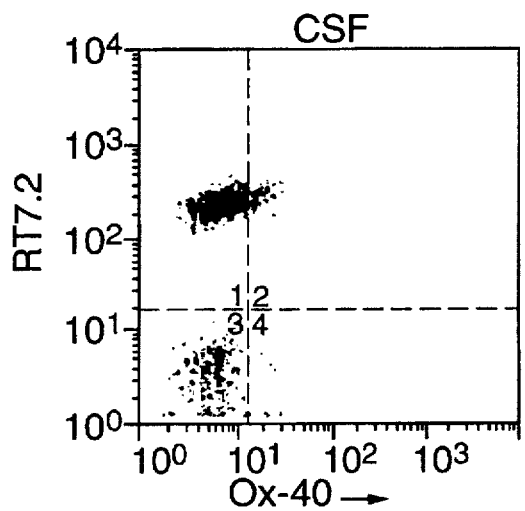
Figure 1D:
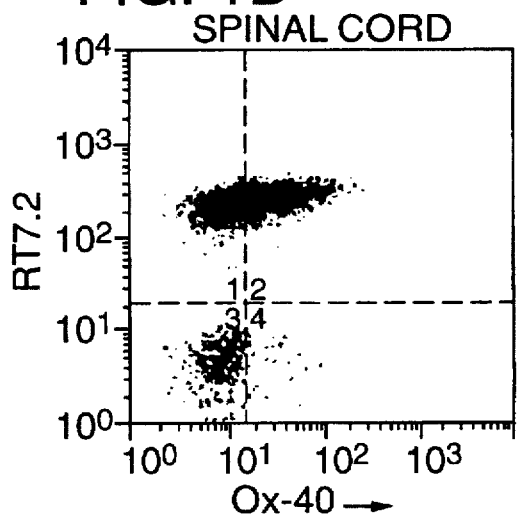

The present invention provides, for the first time, a method of eliminating undesired immune responses caused by antigen activated CD4$^+$ T-cells. The invention relies on the discoveries that a cell surface antigen, termed the OX-40 antigen, is upregulated solely on activated CD4$^+$ T-cells found at the site of inflammation and that this cell surface antigen appears to be internalized rapidly. Based on this discovery, a therapeutic method has been developed which utilizes antibodies which bind to the OX-40 protein (herein termed OX-40 antibodies) linked to cytotoxins, to destroy cells expressing the OX-40 antigen. This type of therapy will be extremely useful because it is targeted only to the antigen activated CD4$^+$ T-cells while leaving the rest of the CD4$^+$ T-cell repertoire intact.

Activated CD4$^+$ T-cells have been implicated in a number of antigen activated autoimmune diseases, including multiple sclerosis, sarcoidosis, rheumatoid arthritis and autoimmune uveitis, as well as in transplantation rejections. (Swanborg, R. H., 1984; Cush, J. J., and Lipsky, P. E., 1988; Caspi et al, 1988; Cobbold, S. P. et al., 1984.) CD4$^+$ T-cell lymphomas have also been shown to have an activated phenotype (Gootenberg, J. E. et al., 1981). The present invention provides both methods of diagnosis and methods of treatment for these and other conditions mediated by activated CD4$^+$ T-cells.

More particularly, and following the description of relevant materials and methods used in this invention, experimental data obtained during the development of the present invention is presented. These data demonstrate that the OX-40 protein is exclusively expressed at the site of autoimmune inflammation in rats with EAE on the surface of myelin basic protein (MBP) activated CD4$^+$ T-cells. It is further shown that the proliferation of MBP activated CD4$^+$ T-cells can be inhibited in vitro using an OX-40 antibody conjugated with a Ricin dgA cytotoxin. This inhibitory activity is shown not to be limited to MBP activated cells, but also to be effective in inhibiting the proliferation of CD4$^+$ T-cells activated by other antigens, including an antigen derived from *Mycobacterium tuberculosis*. The OX-40 antibody-cytotoxin conjugate is shown to be effective in vivo; use of the conjugate is shown to inhibit the clinical development of EAE. Following this, the cloning of the human OX-40 homolog is presented along with the production of monoclonal antibodies to the human OX-40 protein.

Various examples are presented showing the application of the present invention. Specifically, Example 1 describes preferred methods of producing the human OX-40 cDNA enabled by the present invention. Example 2 describes methods of producing purified human OX-40 protein, and Example 3 describes the production of monoclonal and polyclonal antibodies that recognize the human protein. Example 4 describes the production of immunotoxins, based on these monoclonal antibodies, that are suitable for therapeutic use in humans, and other antibody conjugates suitable for diagnostic use. Example 5 describes the use of human OX-40 monoclonal antibodies in diagnosing activated CD4$^+$ T-cell mediated conditions and Example 6 describes the use of the immunotoxins in therapeutic applications. Example 7 describes kits for the diagnosis and treatment of activated CD4$^+$ T-cell mediated conditions.

MATERIALS AND METHODS

Animals Lewis and Buffalo rats were obtained from Harlan Sprague-Dawley, Inc., Indianapolis, Ind. Twelve week old Lewis females were bred with 12 week old Buffalo male rats to generate the F1 Lewis×Buffalo hybrid animals. These F1 progeny were used at 8 to 12 weeks of age for MBP immunization. The rats were housed under germ-free conditions at the VA Medical Center Animal Care Facility, Portland, Oreg. according to institutional guidelines.

Selection of MBP Specific F1 and Lewis CD4$^+$ Lymphocyte Lines T lymphocyte lines were selected on day 12 after immunization with myelin basic protein (MBP). Details of this procedure were described earlier (Vandenbark, A. A., et al., 1985). Briefly, a lymph node cell suspension was incubated with MBP (30 µg/ml) in RPMI 1640 with 1% autologous rat serum. After 3 days at 37° C. in a 7% $CO_2$ atmosphere the cells were cultured in RPMI with 10% horse serum and IL-2. The T-cell lines were maintained in this medium until the rate of division slowed. At this point (7–14 days after MBP stimulation) the cells were restimulated with 10 µg/ml of MBP presented by irradiated Lewis thymocytes, and subsequently expanded further in IL-2 containing medium.

Adoptive Transfer of EAE Activation of the F1 or Lewis T-cell lines for passive transfer of EAE was carried out in 10 cm$^2$ culture dishes using 5×10$^6$ T-cells, 100×10$^6$ irradiated APC, and 10 µg/ml MBP in 10 ml of medium. After three days of activation the blasts were counted and 5–10×10$^6$ T-cell blasts were injected with the associated APC population i.p. into irradiated (600 rads for the F1 into Lewis transfers) or non-irradiated naive Lewis rats. The naive recipients were irradiated the day before adoptive transfer. The recipient rats were inspected daily, and the clinical signs of disease were recorded and scored as follows EAE: 0=no signs; 1=flaccid tail; 2=ataxia; 3=hindquarter paralysis; 4=quadriplegic/moribund.

Cell Collection Cerebrospinal fluid (CSF) was collected by performing cisterna magna puncture using a 27 ga×⅜" needle with 8" tubing (Abbott Hospitals, Inc., Chicago, Ill.). The CSF was diluted in RPMI 1:4 and viable cell numbers were counted. On average, 100 µl/rat were collected. Samples were excluded if the RBC/WBC ratio exceeded 2:1. The blood was obtained by heart puncture and the lymphocytes were separated on Ficoll-Hypaque as described by Kruisbeek, A. M., 1992. The spleen cells were pushed through a wire mesh screen and the RBCs were lysed by the NH$_4$Cl method (Kruisbeek, A. M. 1992).

Spinal Cord Lymphocyte Isolation Spinal cord mononuclear cells were isolated following a modified version of a published protocol (Bourdette, D. N. et al., 1991). Briefly, spinal cords were isolated by insufflation, washed 3× in RPMI in order to remove any contaminating blood cells, homogenized, and then passed through a wire mesh screen. The cells were then washed and resuspended in isotonic Percoll (80%). For each individual spinal cord a 10 ml step gradient was poured into a 15 ml conical tube. Each step gradient had 100% (2 ml), 80% (4 ml), and 40% (4 ml) isotonic Percoll and the cells were layered as part of the 80% fraction. The interface between the 80/40% Percoll steps was harvested and the cells were directly spun down and washed. The lymphocytes obtained at this interface contained both the resting and blasting populations as assessed by forward scatter. A typical yield of lymphocytes obtained from the spinal cord of animals with EAE was usually 0.5–1.5×10$^6$ cells. Lymphocyte recovery was fairly consistent throughout the disease time course, and decreased during the last day of the recovery phase of EAE to ½ or ⅓ of the maximal cell number.

Fluorescence activated cell sorting (FACS) analysis For the dual fluorescence analysis shown in FIGS. 1A–D and 2A–E, the antibodies used were the RT7.2-PE Ab (Pharmingen, La Jolla, Calif.) and the MRC OX-40-FITC Ab (Pharmingen, La Jolla, Calif.). All the analysis was performed on a FACScan with the FACScan Research Software Version A (Becton Dickenson, San Jose, Calif.) operated according to the manufacturer's instructions.

Antigen Specific Proliferation Assays Proliferation assays were performed in 96-well plates as described previously (Vandenbark, A. A. et al., 1985). Briefly, 2×10$^4$ CD4$^+$T-cells and 1×10$^6$ irradiated thymocytes/well were incubated in RPMI and 1% rat serum along with antigen and varying concentrations of the OX-40 immunotoxin or the toxin alone in a 200 µl volume. The cultures were incubated for 72 hr, the last 18 hr in the presence of 0.5 Bq [$^3$H]-thymidine. The cells were harvested onto glass fiber filters and [$^3$H]-thymidine uptake was assessed by liquid scintillation. Mean cpm were calculated from triplicate wells. The SD from replicate wells varied <10% from the mean values.

OX-40 Immunotoxin Inhibition of EAE Naive Lewis rats were injected with an encephalitogenic dose of MBP specific CD4$^+$ T-cells injected in one flank and injected with the immunotoxin at the same time in the opposite flank. Originally a dose curve for the immunotoxin was set up and the optimal dose was found to be between 300–500 µg/8 week old rat. As controls the same molar amount of the toxin alone (dgA) was given to animals in parallel.

EXPERIMENTAL RESULTS

One of the keys to understanding the mechanism(s) by which autoantigen specific T-cells destroy self-tissue is to study the differences associated with an autoreactive T-cell at the site of inflammation versus a non-inflammatory site. To this end an experimental model system was set up in EAE to detect the cells that cause the disease in vivo.

EAE can be induced by the adoptive transfer of in vitro-activated MBP specific CD4$^+$ T-cells into naive recipient rats. Four days after the transfer the animals start showing the paralytic signs of EAE. To allow detection of the donor population within the host, MBP specific F1 (Lewis×Buffalo) CD4$^+$ T-cells were transferred into naive irradiated Lewis recipients. Lewis and Buffalo rats express allelic variants of an epitope of the CD45 cell surface molecule. These allelic variants are termed RT7.1 (Lewis) and RT 7.2 (Buffalo). The RT7.2 allelic marker can therefore be used to detect the F1 T-cells in Lewis hosts because these cells express both forms of the allele while Lewis rats only express the RT7.1 form of the allele. The CD45 molecule is expressed only on leukocytes and constitutes approximately 10% of the total surface protein.

FIGS. 1A–D show that on the first day of disease onset 50% of the MBP specific transferred population (RT7.2$^+$) was positive for the activation marker OX-40 at the site of inflammation (spinal cord), but the transferred population was negative for this cell surface antigen at the non-inflammatory sites (blood and spleen). This suggested that the OX-40 antigen was expressed on the cell surface of autoreactive CD4$^+$T-cells upon antigen recognition in vivo, because the MBP antigen is present in the spinal cord but not in the blood or spleen. The highest expression of the OX-40 antigen on the donor population isolated from the spinal cord was on the day before clinical signs of EAE and as the disease progressed this cell surface molecule went away (FIGS. 2A–E). Therefore, the OX-40 antigen is shown to be expressed in vivo on antigen activated CD4$^+$ T-cells and, furthermore, this antigen is shown to be exclusively expressed on the cells at inflammatory sites where the antigen is present (OX-40 is not expressed on cells at non-inflammatory sites in the absence of antigen). These results (the transient nature and target organ expression of the OX-40 marker) suggested that OX-40 may be a suitable target for antibody mediated deletion of activated autoimmune CD4$^+$ T-cells.

The deletion of selective subsets of lymphocytes can be mediated by antibodies in vivo. Several groups have shown that antibodies linked to toxic molecules (termed immunotoxins) can deplete cell populations expressing the appropriate antigen (Fulton, R. J., et al. 1988). The advantage of immunotoxins is that they are highly selective in their target cell specificity and that small doses can eliminate unwanted/potentially harmful cells.

A variety of cytotoxins can be used to produce immunotoxins. Ricin A chain-antibody conjugates have been used to delete both normal and neoplastic lymphocytes in vivo and in vitro (Fulton, R. J. et al., 1988; Street, N. E. et al., 1987). Other toxins such as Pseudomonas exotoxin A and diphtheria toxin have also been conjugated to antibodies and used to kill specific populations of cells (May, R. D., and Fulton, R. J. 1992).

In the late 1980s and early '90s several human Phase I/II clinical trials were performed using antibodies conjugated to the Ricin A chain (Weiner, L. M., et al. 1989; Spliter, L. E., et al., 1987; Vitetta, E. S., et al., 1991). Most of the trials have involved using antibodies specific for cancer antigens in order to lower the tumor burden in cancer patients. Recently, there has been a development of "second generation" immunotoxins which have avoided some of the problems of non-specific immunogenicity and toxicity in the treated patients. This strategy uses the deglycosylated form of the Ricin A (dgA) chain conjugated to the tumor specific antibody. One such Phase I study used this modified form of the immunotoxin against B cell lymphomas in 15 patients (Vitetta, E. S., et. al., 1991). Approximately 40% of the patients achieved partial remissions in which their overall tumor burden was reduced by 50% or more. Killing of the tumor cells was rapid occurring within 1 week after completion of the therapy.

All of the in vivo studies presented herein use an OX-40 antibody-dgA conjugate. The antibody ricin A conjugation was performed with a heterobifunctional cross-linker SPDP or SMPT by the method described by May, R. D. and Fulton, R. J. (1992). Briefly, a free amino group on the OX-40 antibody was reacted with the crosslinker and the macromolecule was purified. The purified OX-40 antibody product was then reacted with reduced ricin A chain (which has one free cysteine) and the hybrid molecule was purified.

Figure 3:
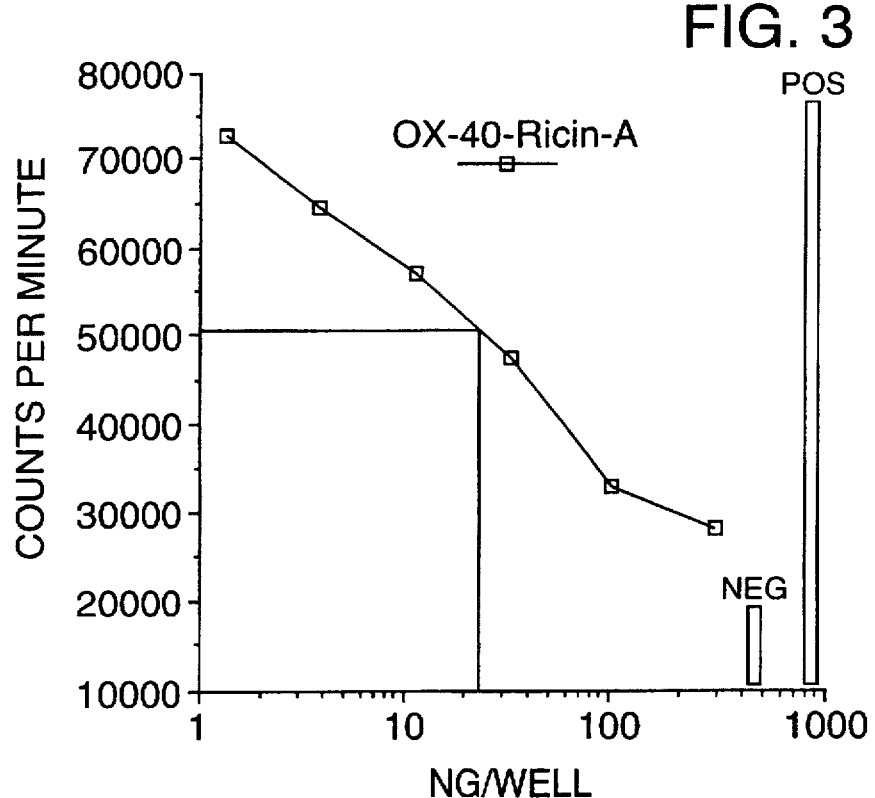
FIG. 3 is a graph showing dose dependent inhibition of antigen specific CD4+ T-cell proliferation by the OX-40-dgA conjugate. Varying concentrations of the OX-40 immunotoxin was added to a constant amount of F1 T-cells, antigen presenting cells (APC), and MBP (myelin basic protein antigen). The open bars (to the right of the graph) show the proliferation (represented by [$^3$H]-thymidine incorporation) of these T-cells with and without antigen with no immunotoxin added (Pos and Neg respectively). The assay was carried out in a 200 µl volume.

Initially the rat OX-40 antibody was conjugated to the dgA form of Ricin and this heteroconjugate was used to inhibit the in vitro proliferation of antigen specific $CD4^+$ T-cell lines. The T-cell lines used were specific for MBP and upon adoptive transfer caused EAE in naive recipients. FIG. 3 shows that the OX-40 heteroconjugate inhibited antigen specific proliferation of the MBP specific T-cell line in a dose dependent manner with 50% inhibition at approximately 20 ng/well. A control using Ricin A alone showed inhibition of the assay only at high concentrations 500 ng/well and above, but no effect on the assay at lower concentrations (data not shown). Controls using the OX-40 antibody alone and an isotype-matched unrelated antibody conjugated to dgA also showed no inhibition (data not shown).

Figure 4A:
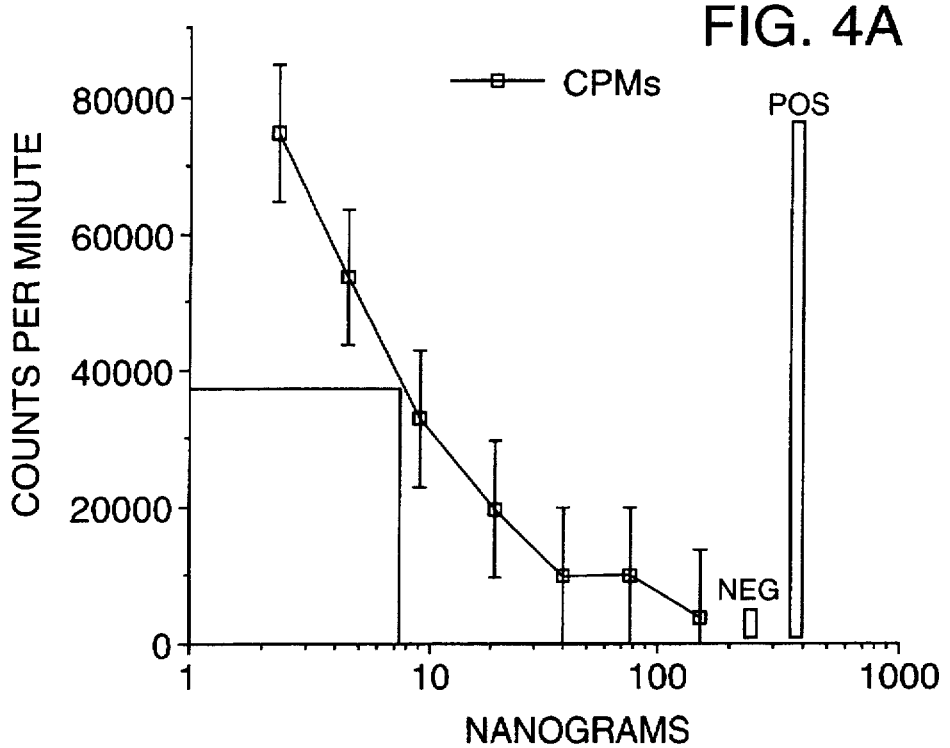
FIGS. 4A–B and FIG. 4B are two graphs showing dose dependent inhibition of antigen specific CD4+ T-cell proliferation by the OX-40-exotoxin conjugate. Varying concentrations of the OX-40-exotoxin was added to a constant amount of F1 T-cells (FIG. 4A) or Lewis T-cells (FIG. 4B), APC, and MBP. The open bars (to the right of the graphs) show the proliferation (represented by [$^3$H]-thymidine incorporation) of these T-cells with and without antigen (Pos and Neg respectively). The assay was carried out in a 200 µl volume.
Figure 4B:
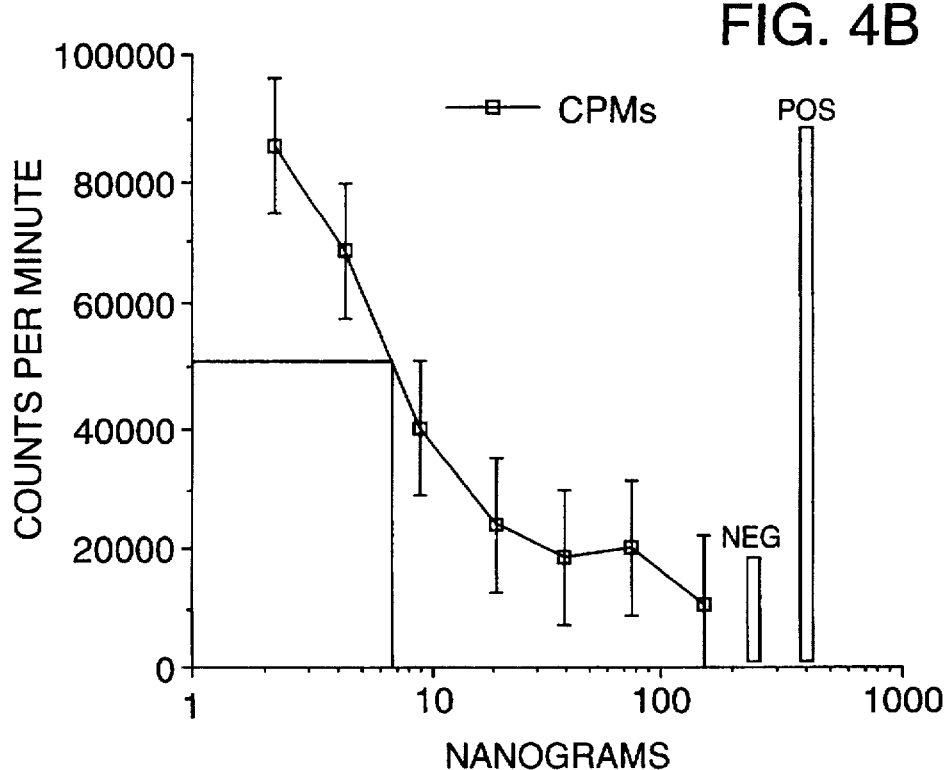

The OX-40 antibody was then conjugated to the Pseudomonas exotoxin and this conjugate was tested for inhibitory effect on antigen specific (MBP) $CD4^+$ T-cell proliferation (FIG. 4). This heteroconjugate was approximately 4-fold more efficient at inhibiting the in vitro assay, and the toxin alone did not inhibit the assay at any concentration. This assay was performed with a Lewis MBP specific line (FIG. 4B) and an F1 (Lewis×Buffalo) MBP specific line (FIG. 4A) with the same results, showing that the inhibition of proliferation was not strain specific.

Figure 5:
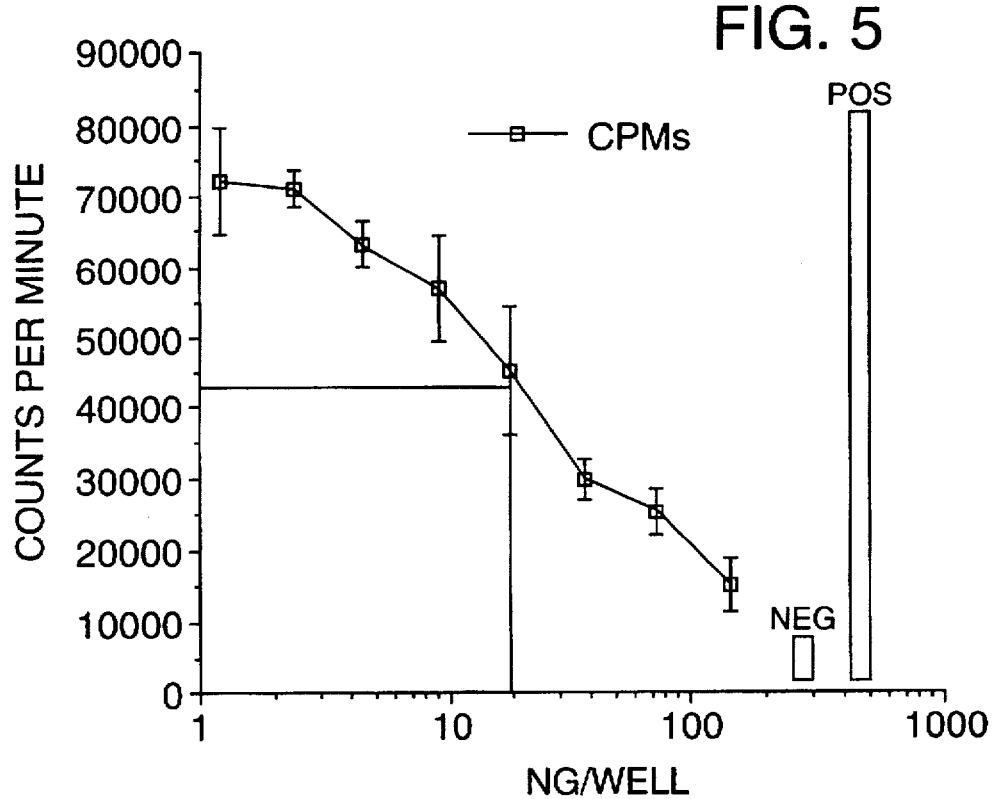
FIG. 5 is a graph showing dose dependent inhibition of PPD antigen specific CD4$^+$ T-cell proliferation by the OX-40-dgA conjugate. Varying concentrations of the OX-40 immunotoxin was added to a constant amount of F1 T-cells, antigen presenting cells (APC), and PPD (antigen). The open bars (to the right of the graph) show the proliferation (represented by [$^3$H]-thymidine incorporation) of these T-cells with and without antigen (Pos and Neg respectively). The assay was carried out in a 200 µl volume.

The OX-40-dgA was also used to inhibit the in vitro proliferation of a $CD4^+$ T-cell line activated with an antigen that was irrelevant to EAE or autoimmunity. The antigen used was the purified protein derivative (PPD) antigen from *Mycobacterium tuberculosis*. This antigen was used to ascertain whether the OX-40 antigen was specific to $CD4^+$ T-cells activated by the MBP antigen, or whether it is present on the surface of all antigen activated $CD4^+$ T-cells regardless of T-cell receptor specificity. As shown in FIG. 5, there was a dose dependent inhibition of proliferation of the PPD activated T-cell line with a comparable 50% inhibition to the MBP activated lines. This shows that the OX-40 immunotoxin will inhibit proliferation of any activated $CD4^+$ T-cell line regardless of the antigen specificity.

Since the OX-40 immunotoxin was effective at inhibiting the proliferation of MBP specific autoimmune $CD4^+$ T-cells in vitro, experiments were then performed to determine the potential of this immunotoxin to kill MBP specific $CD4^+$ T-cells in vivo. To this end irradiated rats were used initially; these were injected with the OX-40-Ricin A conjugate or Ricin A alone. At the same time these animals received an encephalitogenic dose of MBP specific Lewis T-cells. The effect of irradiation is to deplete the rat's immune system so that it would not recognize and deplete the allelic variant F1 donor T-cells. The use of irradiated rats facilitates the detection of the donor T-cells with the RT7.2 antibody in the host after the transfer of these cells and allows the fate of these transferred cells to be determined (see FIGS. 1A–D, 2A–E, and 6B).

As shown in Table I, experiments 1 and 2, only ⅓ animals receiving the OX-40 immunotoxin showed clinical signs of disease while all 8 animals that received unconjugated Ricin A came down with EAE. The inhibitory effect of the immunotoxin appeared to be mediated by the OX-40 anti-body since the Ricin A chain alone showed the same disease score when compared to animals injected with encephalitogenic $CD4^+$ T-cells alone (data not shown).

TABLE I

OX-40 Ricin A Immunotoxin Effect on Experimental Autoimmune Encephalomyelitis

| Transfer Dose[a] | Treatment[b] | Incidence | Day of Onset | EAE Score[c] |
|---|---|---|---|---|
| Exp 1 | | | | |
| $6.5 \times 10^6$ | OX-40-Ricin A | 1/3 | 6 | 0.66 |
| $6.5 \times 10^6$ | Ricin A | 3/3 | 4 | 6.33 |
| Exp 2 | | | | |
| $10 \times 10^6$ | OX-40-Ricin A | 0/5 | — | — |
| $10 \times 10^6$ | Ricin A | 5/5 | 5 | 4.90 |
| Exp 3 | | | | |
| $10 \times 10^6$ | OX-40-Ricin A | 0/2 | — | — |
| $10 \times 10^6$ | No treatment | 3/3 | 4 | 6.50 |

[a]MBP specific $CD4^+$ T-cells were stimulated for 3 days in vitro with antigen and antigen presenting cells and transferred into naive recipients.
[b]400 µg of OX-40-Ricin A or the same molar amount of Ricin A alone was injected at the same time the cells were transferred.
[c]Value represents the mean cumulative EAE score for each group. 0, no signs; 1, limp tail; 2, hind leg weakness; 3, hind quarter paralysis; 4, moribund.

Figure 6A:
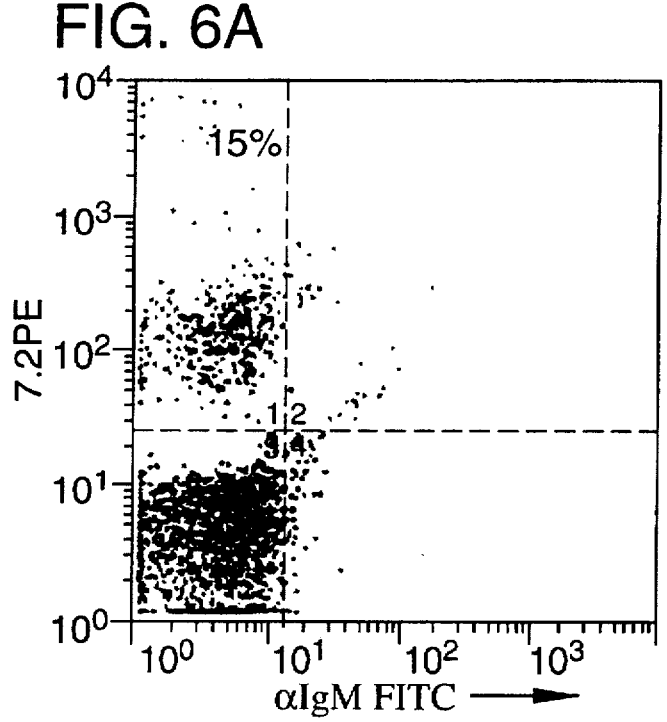
FIGS. 6A–B are two dot plots from a FACS apparatus showing characterization of lymphocytes isolated from the spinal cord of rats that had been treated with a 400 µg dose of OX-40-dgA (FIG. 6A) or untreated rats (FIG. 6B). F1 MBP specific CD4$^+$ T-cells were transferred into irradiated Lewis recipients and OX-40-dgA was given on the same day of transfer. The transfer population was detected by the RT7.2 antibody conjugated to PE (represented on the y-axis) and counterstained with the control antibody anti-rat IgM-FITC.
Figure 6B:
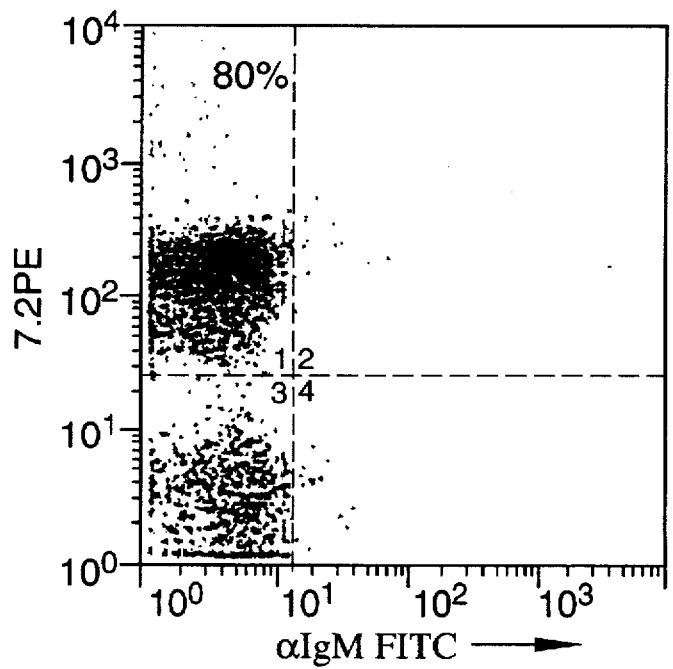

The data in Table I was generated using the EAE model where F1 MBP T-cell lines (Lewis×Buffalo) were injected into irradiated Lewis (parental host) recipients. Thus, the transferred T-cell population could be detected in the spinal cord of these animals with the RT7.2 (Buffalo) antibody. FIGS. 6A and 6B show the outcome of the OX-40-dgA treatment as assessed by the number of donor cells isolated from the spinal cord of the treated (clinically well) and control groups (paralyzed) on the first day of disease onset. A total of 200,000 spinal cord lymphocytes was isolated from the control group and 80% were found to be donor derived. In contrast 80,000 spinal cord lymphocytes was isolated from the control group and only 15% were found to be donor derived. There was over a log-fold difference in the total amount of donor derived MBP reactive $CD4^+$ T-cells isolated from the spinal cord (the inflammatory site) between the two groups (160,000 vs. 12,000). This suggested that OX-40 dGA conjugate was specifically deleting activated $CD4^+$ T-cells in vivo.

The same in vivo experiments were then performed in a non-irradiated host; a Lewis MBP activated T-cell line was transferred into a Lewis host. The non-irradiated host was used because this host has an intact immune system more similar to human patients suffering from these same types of autoimmune diseases. In these experiments it was initially observed that a single injection of the conjugate at the time of transfer of T-cells only partially inhibited subsequent development of the disease. Therefore experiments were performed utilizing two injections at different time intervals. Table II shows that the most effective regime was administration of immunotoxin on the same day as activated T-cells were transferred (day 0) and an additional treatment on the day before disease onset (day 3).

TABLE II

OX-40-Ricin A Immunotoxin Effect on Experimental Autoimmune Encephalomyelitis (in non-irradiated host)

| Transfer Dose[a] | Treatment[b] | Days of Injection | Day of Onset | EAE Score[c] |
|---|---|---|---|---|
| $7.5 \times 10^6$ | OX-40-Ricin A | oam/opm | 4 | 6.50 |
| $7.5 \times 10^6$ | OX-40-Ricin A | 0/1 | 5 | 2.50 |
| $7.5 \times 10^6$ | OX-40-Ricin A | 0/3 | 4 | 0.75 |
| $7.5 \times 10^6$ | OX-40-Ricin A | 0/4 | 4 | 8.50 |

[a]Lewis MBP specific CD4+ T-cells were stimulated for 3 days in vitro with antigen and antigen presenting cells and transferred into Lewis recipients.
[b]300 μg of OX-40-Ricin A was injected at the same time the cells were transferred and a second injection described above.
[c]Value represents the mean cumulative EAE score for each group. 0, no signs; 1, limp tail; 2, hind leg weakness; 3, hind quarter paralysis; 4, moribund.

The day 0/3 injection regimen was repeated for a group of three animals and compared to 3 control animals with similar results (Table III). These results suggest that the immunotoxin was recognizing and killing the autoimmune T-cells at the site of inflammation on day 3 because, (1) the only donor T-cells expressing the OX-40 antigen on day 3 (the day before disease onset) were in the spinal cord compartment (FIGS. 1A–D) and (2) the highest percentage of OX-40 expression on donor T-cells in the spinal cord was the day before disease onset (FIGS. 2A–E).

TABLE III

OX-40-Ricin A Immunotoxin Effect on Experimental Autoimmune Encephalomyelitis (in non-irradiated host)

| Transfer Dose[a] | Treatment[b] | Days of Injection | Day of Onset | EAE Score[c] |
|---|---|---|---|---|
| $9.0 \times 10^6$ | OX-40-Ricin A | 0/3 | 5 | 1.33 |
| $9.0 \times 10^6$ | Nothing | — | 4 | 8.25 |

[a]Lewis MBP specific CD4+ T-cells were stimulated for 3 days in vitro with antigen and antigen presenting cells and transferred into Lewis recipients.
[b]400 μg of OX-40-Ricin A or the same molar amount of Ricin A alone was injected at the same time the cells were transferred.
[c]Value represents the mean cumulative EAE score for each group of 3 animals. 0, no signs; 1, limp tail; 2, hind leg weakness; 3, hind quarter paralysis; 4, moribund.

The conclusion from the data presented is that the OX-40 immunotoxin is extremely effective at killing/inhibiting antigen specific CD4+ T-cell function both in vitro and in vivo. The effect of this specific immunotoxin does not seem to be restricted by strain or antigen specificity and will most likely have a wide range of applications in vivo.

The experiments described in Examples 1–4 above were performed using the rat model system and antibodies against the rat OX-40 protein. However, the rat OX-40 antibody does not recognize human or murine activated CD4+ T-cells (data not shown). To facilitate the development of the present invention for human therapeutic use, it is necessary to produce antibodies against the human OX-40 protein.

To that end, a human cDNA encoding the human OX-40 homolog was cloned. Initially, two oligonucleotide primers were synthesized for use in the polymerase chain reaction (PCR). These primers were designed to amplify the full length OX-40 cDNA sequence; one primer was homologous to the coding strand in the region of the start codon of the rat cDNA sequence and the other was the inverse complement of the coding strand in the region of the stop codon of the rat cDNA sequence. Surprisingly, no product was ever obtained when these PCR primers were used with RNA isolated from activated CD4+ T lymphocytes from humans.

Since the standard method of cloning the human OX-40 cDNA was unsuccessful, an alternative approach was required. First, the PCR primers were successfully used to clone the murine OX-40 cDNA by PCR from RNA isolated from murine CD4+ T-cells activated with Concanavalin A (data not shown). Then, the murine OX-40 cDNA was used to probe a cDNA lambda gt11 library from human activated T lymphocytes (No. HL10316 purchased from Clontech, Palo Alto, Calif.). Five similarly sized positive clones (1050–1200 bp) were obtained. These five recombinant lambda clones were subcloned into the Bluescript plasmid (Stratagene, La Jolla) and then sequenced on the 370A automated sequencer (Applied Biosystems, Pasadena Calif.). The sequence of the human OX-40 cDNA is set forth in SEQ. ID No. 1 in the accompanying sequence listing and is shown in FIG. 7.

A comparison of the predicted amino acid sequence of the human OX-40 protein with peptide sequences in the Genbank database indicated a high degree of homology with the murine OX-40 and rat OX-40 sequences; the probabilities that the predicted amino acid sequence of the human OX-40 protein shown in Seq. I.D. No. 1 was not related to the murine or rat OX-40 amino acid sequences were predicted to be $3.4 \times 10^{-58}$ and $2.9 \times 10^{-56}$ respectively. The next most closely related peptide sequence gave a probability of $1.1 \times 10^{-11}$. Furthermore, a comparison of the homologies between the human and rat OX-40 cDNA and amino acid sequences over a 64 amino acid (192 base pair) region starting at amino acid 31 of the rat sequence revealed an amino acid homology of 62.5% and a nucleotide homology of 67.5%. All ten cysteine residues within this 64 amino acid stretch were conserved.

EXAMPLE ONE

Having herein provided the sequence of the human OX-40 cDNA, one skilled in the art will recognize that the full length cDNA clone can now readily be obtained by standard methods. Such methods include, for example, the polymerase chain reaction (PCR) by which means DNA sequences can be amplified. Methods and conditions for PCR amplification of DNA are described in Innis et al. (1990) and Sambrook et al. (1989).

The selection of PCR primers for amplification of the human OX-40 cDNA will be made according to the portions of the cDNA which are desired to be amplified. Primers may be chosen to amplify small fragments of the cDNA or the entire cDNA molecule. Variations in amplification conditions may be required to accommodate primers of differing lengths; such considerations are well known in the art and are discussed in Innis et al. (1990). By way of example only, the entire cDNA molecule corresponding to the human OX-40 cDNA may be amplified using the following primers. Primers 1 and 2 are also set forth in the accompanying sequence listing as SEQ I.D. Nos. 2 and 3, respectively.

Primer 1: 5' ATGTGCGTGGGGGCTCGGCGGCTG 3' SEQ ID NO.2

Primer 2: 5' TCAGAACTTGACCAGGGTGGAGTG 3' SEQ ID NO.3

Template DNA for PCR amplification to produce the human OX-40 cDNA can be extracted from the lambda GT11 cDNA library from human activated T lymphocytes produced by Clontech, Palo Alto, Calif. (Catalog No. HL10316).

Alternatively, the human OX-40 cDNA may be obtained by PCR amplification of reverse transcribed RNA (RT-PCR)

(Veres et al., 1987; Kawasaki et al., 1990). Essentially, total RNA is extracted from activated human CD4 T-cells by any one of a variety of methods routinely used as described in Sambrook et al. (1989) and Ausubel et al. (1987). Suitable human CD4 T-cells include the human CD4$^+$ T-cell lymphoma cell line described by Gootenberg et al. (1981). Alternatively, activated CD4$^+$ T-cells can be isolated from human peripheral blood as described by Kruisbeek (1992). The extracted RNA is then used as a template for performing RT-PCR amplification of the human OX-40 cDNA.

Standard methods for the purification and cloning of PCR products are well known in the art and are described by Innis et al. (1990) and Sambrook et al. (1989).

EXAMPLE TWO

With the provision of the human OX-40 cDNA, the expression and purification of the human OX-40 protein by standard laboratory techniques is now enabled. The purified protein may be used for antibody production and patient therapy.

Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification of the human OX-40 protein. For example, fusion proteins consisting of amino terminal peptides encoded by a portion of the *E. coli* lacZ or trpE gene linked to the part or all of the human OX-40 protein may be used to prepare polyclonal and monoclonal antibodies that recognize the human OX-40 protein. Intact, native proteins may also be produced in *E. coli* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17). Vector systems suitable for the expression of lacZ fusion genes include the pUR series of vectors (Ruther and Muller-Hill, 1983), pEX1-3 (Stanley and Luzio, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). Human OX-40 fusion proteins may be isolated from protein gels, lyophilized, ground into a powder and used as antigen preparations.

For expression in mammalian cells, the cDNA sequence may be ligated to heterologous promoters, such as the simian virus (SV)40 promoter in the pSV2 vector (Mulligan and Berg, 1981), and introduced into cells, such as monkey COS-1 cells (Gluzman, 1981), to achieve transient or long-term expression. The cDNA sequence (or portions derived from it) or a mini gene (a cDNA with an intron and its own promoter) is introduced into eukaryotic expression vectors by conventional techniques. These vectors are designed to permit the transcription of the cDNA eukaryotic cells by providing regulatory sequences that initiate and enhance the transcription of the cDNA. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982). The level of expression of the cDNA can be manipulated with this type of vector, either by using promoters that have different activities (for example, the baculovirus pAC373 can express cDNAs at high levels in *S. frugiperda* cells (Summers and Smith, 1985)) or by using vectors that contain promoters amenable to modulation, for example, the glucocorticoid-responsive promoter from the mouse mammary tumor virus (Lee et al., 1982).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

The human OX-40 protein expressed in eukaryotic cells may be purified and used to produce antibodies. The human OX-40 protein may be extracted following release of the protein into the supernatant, or, the cDNA sequence may be incorporated into a eukaryotic expression vector and expressed as a chimeric protein with, for example, β-globin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene, La Jolla, Calif.). This vector encodes rabbit β-globin.

This invention encompasses recombinant cloning vectors containing the human OX-40 cDNA sequence, or portions thereof. The human OX-40 cDNA is operatively linked in the vector to an expression control sequence in the recombinant DNA molecule so that the human OX-40 polypeptide, or a portion thereof, can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli*, Pseudomonas, *Bacillus subtilis, Bacillus stearothermophilus* or other bacilli; other bacteria; yeast; fungi; insect; mouse or other tissue cells, including human tissue culture cells.

In a preferred embodiment of the present invention, the full length human OX-40 cDNA as shown in FIG. 7 (from start codon to stop codon) is ligated into a baculovirus vector and the recombinant human protein is produced in the appropriate insect cells. Suitable baculovirus expression systems include the BacPAK™ Baculovirus Expression System produced by Clontech (Palo Alto, Calif.). Thus, by way of example, the full length human OX-40 cDNA is ligated into the plasmid pBacPAK1 and expressed in *Spodoptera fugiperda* cells according to the manufacturer's instructions.

The human OX-40 protein produced in the insect cells is then purified by standard techniques. A preferred technique of isolating the recombinant product is to use a vector that adds an additional 6 residues of histidine to the recombinant protein. Fusion proteins produced in this manner chelate metal, which facilitates protein purification enormously. Thus, for example, in high salt, polyhistidine fusion proteins bind with a high affinity to a metal chelate matrix whereas the majority of host proteins do not bind at all. Low affinity binding host proteins can be washed off the matrix by decreasing the pH to 6.0. Specific elution of the polyhistidine-containing fusion protein can be accomplished with 300 mM imidazole buffer at pH 6.0.

EXAMPLE THREE

Monoclonal antibodies may be produced to the human OX-40 protein for therapeutic use. Substantially pure human OX-40 protein suitable for use as an immunogen is isolated from the transfected or transformed cells as described in Example 2 above. Concentration of protein in the final preparation is adjusted, for example, by concentration on an Amicon filter device, to the level of a few milligrams per milliliter. Monoclonal antibody to the protein can then be prepared as follows:

A. Monoclonal Antibody Production by Hybridoma Fusion.

Monoclonal antibody to epitopes of the human OX-40 protein identified and isolated as described can be prepared from murine hybridomas according to the classical method of Kohler and Milstein (1975) or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

B. Antibodies Raised Against Synthetic Peptides.

An alternative approach to raising antibodies against the human OX-40 protein is to use synthetic peptides synthesized on a commercially available peptide synthesizer based upon the predicted amino acid sequence of the human OX-40 protein shown in FIG. 7.

In a preferred embodiment of the present invention, monoclonal antibodies that recognize the human OX-40 protein are produced. Optimally, monoclonal antibodies raised against the human OX-40 protein specifically detect the human OX-40 protein. That is, such antibodies recognize and bind the human OX-40 protein and do not substantially recognize or bind to other proteins found in human cells. Put another way, such antibodies have a specificity of binding in humans to substantially only the human OX-40 protein and thus to substantially only activated $CD4^+$ T-cells.

The determination that an antibody specifically detects the human OX-40 protein is made by any one of a number of standard immunoassay methods; for instance, the Western blotting technique (Sambrook et al., 1989). To determine that a given antibody preparation (such as one produced in a mouse) specifically detects the human OX-40 protein by Western blotting, total cellular protein is extracted from human cells that do not express the OX-40 antigen, such as non-activated lymphocytes. As a positive control, total cellular protein is also extracted from activated $CD4^+$ T-cells. These protein preparations are then electrophoresed on a sodium dodecyl sulfate-polyacrylamide gel. Thereafter, the proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the human OX-40 protein will, by this technique, be shown to bind to the human OX-40 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-human OX-40 protein binding. Preferably, no antibody would be found to bind to proteins extracted from the unactivated $CD4^+$ T-cells.

In addition to binding assays using extracted proteins, monoclonal antibodies raised against the human OX-40 protein are tested to confirm their ability to recognize the appropriate cell type (activated $CD4^+$ human T-cells) by conjugating the human OX-40 antibody to a fluorescent tag (such as FITC) and analyzing cell populations by FACS as described above. The human OX-40 antibody will preferably recognize activated $CD4^+$ T-cells. Therefore, dual staining of an activated T-cell population with CD4-PE and OX-40-FITC should show cells that are double positive. In contrast, activated T-cells stained with CD8-PE and OX-40-FITC should show a population that is single positive for the OX-40 antigen; that is, the OX-40 antibody should not recognize CD8$^+$ T-cells.

Monoclonal antibodies for use in the present invention will generally be of the IgM or IgG isotype, and will preferably be of mouse, human or other mammalian origin.

In one preferred embodiment of the present invention, the monoclonal antibodies that recognize the human OX-40 antigen are mouse monoclonal antibodies that have been "humanized". Such humanized antibodies can be more safely administered to human patients than can unmodified monoclonal antibodies produced in mouse cells. Monoclonal antibodies produced in non-human cells, such as mouse cells, generally evoke an immune response when administered to a human host, thus limiting the duration of the biological efficacy of the monoclonal antibody (see generally, U.S. Pat. No. 4,731,244 and WO 89/06976). Humanized antibodies are produced by recombinant DNA technology and generally comprise the antibody constant region from human monoclonal antibodies combined with the variable (antigen recognition) region from the mouse monoclonal antibody that recognizes the target antigen (in this case the human OX-40 protein). Because only the variable region is of murine origin, humanized monoclonal antibodies are significantly less likely to induce an immune response when administered to a human patient.

Methods for humanizing antibodies are described by Riechmann et al. (1988). Riechmann et al. introduced the six hypervariable regions from the heavy and light chain domains of a rat antibody into a human IgG1 antibody directed against human lymphocytes. Riechmann et al. showed that this "humanized" antibody was able to bind to its target antigen in vivo without eliciting an anti-immunoglobulin immune response.

For the preferred embodiments of this invention, intact monoclonal antibodies are used. However, one skilled in the art will recognize that portions of monoclonal antibodies that are capable of recognizing and binding to the human OX-40 protein may also be employed. These antibody fragments generally include Fab, F(ab)'$^2$ and Fv fragments of antibodies which recognize the human OX-40 protein. Immunotoxins comprising antibody fragments have been shown to be effective in deleting CD4$^+$ T-cells both in vivo and in vitro using an antibody that recognizes all cells that express the CD4 antigen (Street et al., 1987).

EXAMPLE FOUR

As set forth in the preceding examples, this invention enables the production of monoclonal antibodies that, in humans, bind substantially only the human OX-40 protein. For use of such monoclonal antibodies in therapeutic applications, it will be necessary to conjugate the antibodies to a cytotoxic moiety. Such conjugates are commonly referred to as immunotoxins. Immunotoxins are characterized by two components; a cytotoxic agent which is usually fatal to a cell when attached or absorbed, and a "delivery vehicle" which serves to deliver the cytotoxin to the target cell type. For the present invention, the target cell type is activated CD4$^+$ T-cells and the delivery vehicle is an antibody or antibody fragment that recognizes and binds to the human OX-40 antigen, as described in Example 8 below.

A number of suitable cytotoxins are known in the art, including: cytotoxic proteins such as the Ricin A chain, the deglycosylated form of the Ricin A chain (dgA), the Pseudomonas exotoxin; radionuclides such as Iodine-131, Yttrium-90, Rhenium-188 and Bismuth-212; and a number of chemotherapeutic drugs such as vindesine, methotrexate, adriamycin and cis-platinum. (See generally, Olsnes and Phil (1982), and Baldwin and Byers (1985)). In one embodiment of the present invention, the cytotoxin is the deglycosylated form of the Ricin A chain, as described in U.S. Pat. No. 4,590,071.

A selected cytotoxin may be conjugated with an anti-human OX-40 antibody to produce an immunotoxin for use in the present invention. Antibodies may be conjugated with cytotoxins by a number of well known procedures, as generally described in Thorpe et al. (1982). For example, where the cytotoxic agent is a protein (such as the Ricin A chain) and the delivery vehicle is an intact monoclonal antibody, the linkage may be by way of heterobifunctional cross linkers, such as carbodiimide or gluteraldehyde. Preferred methods of producing immunotoxins using the deglycosylated Ricin A chain are provided in U.S. Pat. No. 4,590,071, and WO 89/06967, which are herein incorporated by reference.

Immunotoxins as provided by the present invention and produced as described above are subsequently tested to confirm their in vitro efficacy. Such in vitro testing is performed using human CD4$^+$ T-cells and the methods described above. For example, an immunotoxin produced according to the present invention (i.e. a cytotoxin conjugated to a monoclonal antibody that has been shown to be specific to the human OX-40 protein), is tested using in vitro inhibition studies on MBP specific CD4$^+$ T-cell lines from multiple sclerosis patients. Immunotoxins potentially suitable for use in human therapy are those capable of inhibiting the in vitro proliferation of such cells.

Since these immunotoxins are capable of inhibiting the in vitro proliferation of activated CD4$^+$ T-cells from multiple sclerosis patients, they should be capable of inhibiting the proliferation of all activated CD4$^+$ T-cells, regardless of origin. This conclusion is supported by the evidence set forth above, where the rat Ox-40-dgA immunotoxin was shown to be effective against MPB activated rat CD4$^+$ T-cells and PPD activated rat CD4$^+$ T-cells. To confirm that the human OX-40 immunotoxin has this general activity, similar in vitro proliferation studies as described above may also be performed with human CD4$^+$ T-cells specific for other antigens (such as herpes simplex virus.)

In an alternative embodiment of the present invention described in Example 5 below, anti-human OX-40 antibodies can also be used to diagnose conditions mediated by activated CD4$^+$ T-cells. For such applications, it is preferable that the antibody is conjugated to a suitable chemical "tag" which facilitates detection of the antibody. Suitable molecules include the fluorescent molecules fluorescein isothiocyanate (FITC) and R-phycoerythrin (PE) as utilized in the present invention.

EXAMPLE FIVE

In one embodiment of the present invention, monoclonal antibodies that specifically bind the human OX-40 protein are used to detect conditions mediated by activated CD4$^+$ cells. For such purposes, human OX-40 antibodies are conjugated with other molecules, such as fluorescent markers.

Biopsy samples are taken from inflamed tissue for analysis. One skilled in the art will recognize that the source of the biopsy sample will vary between different conditions. In the case of multiple sclerosis the lymphocytes will be isolated from the CSF, while in rheumatoid arthritis the lymphocytes will be isolated from the synovial fluid of inflamed joints. In the case of transplant rejection biopsies will be taken directly from the target organ during a rejection episode.

In a preferred embodiment, a biopsy sample taken from a patient will be fractioned into a lymphocyte fraction (by methods described earlier; see Materials and Methods). The purified lymphocytes will be stained with the OX-40-FITC antibody and the percentage of positive lymphocytes will be quantitated on a FACScan apparatus. This percentage will be compared with the percentage found in healthy individuals. Any statistically significant increase will provide an early indication of an inflammatory event and will lead to early diagnosis of autoimmune disorders.

EXAMPLE SIX

For therapeutic applications, such as treatment of autoimmune inflammations associated with multiple sclerosis, it is anticipated that the presence of activated $CD4^+$ T-cells at the site of inflammation will be established before treatment is commenced. The presence of these cells can be established using the diagnostic methods described in Example 5 above. If the diagnostic test produces a result indicating the presence of activated $CD4^+$ T-cells at the inflammatory site, then therapeutic application of the immunotoxin is appropriate.

For therapeutic administration of the immunotoxins for treatment of conditions mediated by activated $CD4^+$ T-cells, standard published protocols that set forth treatment regimes using immunotoxins may be utilized. These include protocols described by Vitetta et al., 1991, and in WO89/06967. These documents are herein incorporated by reference.

In general, the method of treating a patient suffering from a condition mediated by antigen-activated $CD4^+$ T-cells will comprise administering to the patient an effective amount of an antibody (or a portion of an antibody) conjugated with a cytotoxic agent wherein the antibody (or the portion of the antibody) recognizes and binds to the human OX-40 antigen. As discussed above, antibodies and portions of antibodies conjugated with a cytotoxic agent are commonly referred to as immunotoxins. Effective amounts of these immunotoxins may generally be referred to as a suitable dose of an immunotoxin.

One skilled in the art will recognize that any dose of the immunotoxins greater than zero will have some effect on the activated $CD4^+$ T-cell population in a patient. However, suitable doses are limited by the onset of adverse side effects of high doses of immunotoxin. As described in WO89/06967, for immunotoxins comprising a monoclonal antibody conjugated with the ricin A chain, suitable doses are in the range of 0.05–1.0 mg/kg daily for up to 14 days. As described by Vitetta et al. (1991), for immunotoxins comprising antibody fragments (such as the Fab' fragment) linked to the chemically deglycosylated ricin A chain, doses will preferably be in the range of 25–150 mg/m².

EXAMPLE SEVEN

One embodiment of the present invention is a kit containing monoclonal antibodies that recognize the human OX-40 antigen. Such a kit would comprise a container within which the monoclonal antibody is contained.

In one embodiment of such a kit, the kit would contain the monoclonal antibody in a form conjugated with a cytotoxin, such as dgA, whereby the kit could be used to treat patients suffering from a condition mediated by activated $CD4^+$ T-cells. This antibody-cytotoxin conjugate would preferably be provided in a form suitable for administration to a patient by injection. Thus, the kit might contain the antibody-cytotoxin conjugate in a suspended form, such as suspended in a suitable pharmaceutical excipient. Alternatively, the conjugate could be in a solid form suitable for reconstitution.

In an alternative embodiment, the kit would contain the monoclonal antibody in a form suitable for diagnostic use, such as conjugated to a fluorescent marker. Such kits would be used in the detection of inflammatory conditions mediated by activated $CD4^+$ T-cells.

The foregoing examples are illustrative of the present invention, but are not limiting. Numerous variations and modifications on the invention as set forth can be effected without departing from the spirit and scope of the present invention.

REFERENCES

Ahmad et al. (1986). *J. Virol.* 57:267.

Amann and Brosius (1985). *Gene* 40:183.

Alt et al. (1978). *J. Biol. Chem.* 253:1357.

Baldwin and Byers (Eds.) (1985). "Monoclonal Antibodies for Cancer Detection and Therapy," pp. 159–179; 224–266.

Bernstein et al. (1985). *Gen. Engr'g* 7:235.

Birkeland, M. L., and A. N. Barclay (1992). Abstract: *8th International Congress of Immunology* W-18(1):82.

Bourdette, D. N. et al. (1991). *J. Neurosci. Res.* 30:308–315.

Brash et al. (1987). *Mol. Cell Biol.* 7:2013.

Caspi, R. R. et al. (1988). *J. of Immunol.* 140:1490–1495.

Cobbold, S. P. et al. (1984). *Nature* 312:548–552.

Cush, J. J., and Lipsky, P. E. (1988). *Arthritis and Rheumatism* 31(10):1230–1238.

Engvall (1980). *Enzymol.* 70:419.

Felgner et al. (1987). *Proc. Natl. Acad. Sci USA* 84:7413.

Fulton, R. J. et al. (1988). *Cancer Research* 48:2626–2631.

Gluzman (1981). *Cell* 23:175–182.

Gootenberg, J. E. et al. (1981). *Journal of Experimental Medicine*, 154:1403–1418.

Graham and vander Eb (1973). *Virology* 52:466.

Gray et al. (1982). *Proc. Natl. Acad. Sci. USA* 79:6598.

Gorman et al. (1982). *Proc. Natl. Acad. Sci USA* 78:6777–6781.

Harlow and Lane (1988). *Antibodies, A Laboratory Manual*, Cold Spring Harbor Laboratory, New York.

Innis et al. (Eds.) (1990). *PCR Protocals, A Guide to Methods and Applications*, Academic Press, Inc., San Diego, Calif.

Klein et al. (1987). *Nature* 327:70.

Kohler and Milstein (1975). *Nature* 256:495.

Kawasaki et al. (1990). In *PCR Protocols, A Guide to Methods and Applications*, Innis et al. (eds.), 21–27, Academic Press, Inc. San Diego, Calif.

Kruisbeek, A. M. (1992). *Current Protocols in Immunology* (J. E. Coligan, A. M. Kruisbeek, D. H. Margulies, E. M. Shevach, and W. Strober, eds.) pp. 3.1.3–3.1.5. Greene Publishing and Wiley-Interscience, New York.

Lee et al. (1982). *Nature* 294:228.

Mallett, S. et al. (1990). *EMBO* 9(4):1063–1068.

May, R. D., and Fulton, R. J. (1992). *In Vitro Methods of Toxicology* (R. R. Watson, editor) pp. 9–20. CRC Press Inc., Boca Raton, Fla.

McCuthan et al. (1968). *J. Natl Cancer Inst.* 41:351.

Mueller et al. (1978). *Cell* 15:579.

Mulligan and Berg (1981). *Proc. Natl. Acad. Sci. USA* 78:2072–2076.

Mulligan et al. (1981). *Proc. Natl. Acad. Sci. USA* 78:1078–2076.

Neumann et al. (1982). *EMBO J* 1:841.

Oksenberg, J. R. et al. (1993). *Nature* 362:68–70.

Oksenberg, J. R. et al. (1990). *Nature* 345:344–345.

Olsnes and Phil. (1982). "Chimeric Toxins", *Pharm. Therap.* 25:355–381.

Riechmann et al. (1988). *Nature* 332:323–327.

Ruther and Muller-Hill (1983). *EMBO J.* 2:1791.

Sambrook et al. (1989). In *Molecular Cloning: A Laboratory Manual*, Cold Spring Harbor, N.Y.

Sarver et al. (1981). *Mol. Cell Biol.* 1:486.

Schafner (1980). *Proc. Natl. Acad. Sci. USA* 77:2163–2167.

Shimatake and Rosenberg (1981). *Nature* 292:128.

Southern and Berg (1982). *J. Mol. Appl. Genet.* 1:327–341.

Spaete et al. (1982). *Cell* 30:295.

Spliter, L. E. et al. (1987). *Cancer Research* 47:1717–1723.

Stanley and Luzio (1984). *EMBO J.* 3:1429.

Steinman, L. (1993). *Scientific American* September:107–114.

Street, N. E. et al. (1987). *J. of Immunol.* 139:1734–1738.

Studiar and Moffatt (1986). *J. Mol. Biol.* 189:113.

Sugden et al. (1985). *Mol. Cell Biol.* 5:410.

Summers and Smith (1985). In *Genetically Altered Viruses and the Environment*, Fields et al. (Eds.) 22:319–328. Cold Spring Harbor Laboratory Press, Cold Spring Harbor, N.Y.

Swanborg, R. H. (1983). *J. Immunol.* 130:503–510.

Thorpe et al. (1982). "Monoclonal Antibody-Toxin Conjugates: Aiming the Magic Bullet." *Monoclonal Antibodies in Clinical Medicine*, Academic Press, pp. 168–190.

Vandenbark, A. A. et al. (1985). *J. Immunol.* 135:223–228.

Veres et al. (1987). *Science* 237:415–417.

Vitetta, E. S. et al. (1991). *Cancer Research* 51:4052–4058.

Weiner et al. (1989). *Cancer Research* 49:4062–4067.

---

We claim:

1. A method of treating a human patient suffering from a condition mediated by activated CD4+ T-cells expressing an OX-40 antigen, comprising administering to the patient a therapeutically effective amount of a cytotoxic agent conjugated to an antibody that is capable of binding specifically to a human OX-40 antigen having the amino acid sequence set forth in Seq. I.D. No. 1.

2. The method of claim 1 wherein the antibody is a monoclonal antibody.

3. The method of claim 2 wherein the monoclonal antibody is a humanized monoclonal antibody.

4. The method of claim 1 wherein the patient is suffering from a condition selected from the group consisting of: multiple sclerosis, sarcoidosis, rheumatoid arthritis, autoimmune uveitis, T-cell lymphoma, and rejection of a transplanted organ or tissue.

5. The method of claim 1 wherein the patient is suffering from multiple sclerosis.

6. The method of claim 1 wherein the patient is suffering from sarcoidosis.

7. The method of claim 1 wherein the patient is suffering from rejection of a transplanted organ or tissue.

8. The method of claim 1 wherein the patient is suffering from rheumatoid arthritis.

9. The method of claim 1 wherein the patient is suffering from autoimmune uveitis.

10. The method of claim 1 wherein the patient is suffering from a CD4+ T-cell lymphoma.

11. A method of treating a human patient suffering from a condition mediated by activated CD4+ T-cells expressing an OX-40 antigen comprising administering to the patient a cytotoxic conjugate comprising a Fab, F(ab')$_2$ or Fv fragment of a monoclonal antibody conjugated with a cytotoxic agent and wherein said fragment is capable of binding specifically to an OX-40 antigen having the amino acid sequence set forth in Seq. I.D. No. 1.

12. A method for reducing a population of CD4+ T-cells that express an OX-40 antigen in a human comprising administering an effective amount of an antibody-cytotoxin conjugate wherein the antibody is capable of binding specifically to a human OX-40 peptide having the amino acid sequence shown in Seq. I.D. No. 1.

13. A method of reducing autoimmune inflammation in a human patient suffering from multiple sclerosis, comprising the steps of:

diagnosing an acute autoimmune inflammation in the patient;

administering to the patient a therapeutically effective amount of an immunotoxin wherein said immunotoxin binds specifically to a human OX-40 cell surface antigen having the amino acid sequence set forth in Seq. I.D. No. 1.

14. A method for reducing a population of antigen activated CD4+ T-cells that express an Ox-40 antigen in a human subject comprising administering to the subject a therapeutically effective amount of an antibody capable of binding specifically to a human peptide having an amino acid sequence set forth in Seq. I.D. No. 1.

15. The method of claim 14 wherein the antibody is a monoclonal antibody.

16. The method of claim 15 wherein the monoclonal antibody is a humanized monoclonal antibody.

17. A method for depleting from the body of a human subject CD4+ T-cells that express an Ox-40 antigen, the method comprising administering a therapeutically effective amount of a specific binding agent to the subject wherein the specific binding agent is capable of binding specifically to a human Ox-40 antigen having the amino acid sequence set forth in Seq. I.D. No. 1 and wherein the specific binding agent is selected from the group consisting of monoclonal antibodies, polyclonal antibodies, and fragments of monoclonal antibodies.

18. The method of claim 17 wherein the specific binding agent is a monoclonal antibody.

19. The method of claim 18 wherein the monoclonal antibody is a humanized monoclonal antibody.

20. The method of claim 17 wherein the specific binding agent is a fragment of a monoclonal antibody, said fragment selected from the group consisting of Fab, F(ab')$_2$ and Fv fragments.

21. A method of treating a human patient suffering from a condition mediated by activated CD4+ T-cells expressing an OX-40 antigen, the method comprising administering to the patient a therapeutically effective amount of a specific binding agent selected from the group consisting of antibodies and fragments thereof that specifically bind a human Ox-40 antigen having the sequence set forth in Seq. I.D No. 1.

22. The method of claim 21 wherein the specific binding agent is a monoclonal antibody or a fragment thereof.

23. The method of claim 22 wherein the specific binding agent is a humanized monoclonal antibody or a fragment thereof.

* * * * *

UNITED STATES PATENT AND TRADEMARK OFFICE
CERTIFICATE OF CORRECTION

PATENT NO. : 5,759,546
DATED : June 2, 1998
INVENTOR(S) : Andrew D. Weinberg et al.

It is certified that error appears in the above-identified patent and that said Letters Patent is hereby corrected as shown below:

Col. 4, line 58, "Figs. 4A-B and Fig. 4B" should read --Figs. 4A-B--.

Col. 9, line 62, ", and 6B)." should read --,6A and 6B).--.

Signed and Sealed this

Eighth Day of December, 1998

Attest:

BRUCE LEHMAN

*Attesting Officer*   *Commissioner of Patents and Trademarks*